(12) United States Patent
Gourguillon et al.

(10) Patent No.: US 11,357,719 B2
(45) Date of Patent: Jun. 14, 2022

(54) **METHOD FOR OBTAINING A DIGLYCOSIDE-ENRICHED *ARMERIA MARITIMA* EXTRACT, AND USE THEREOF IN COSMETICS**

(71) Applicants: BIOTECHMARINE, Quemper Guezennec (FR); SOCIETE D'EXPLOITATION DE PRODUITS POUR LES INDUSTRIES CHIMIQUES SEPPIC, Paris (FR); CENTRE NATIONAL DE LA RECHERCHE SCIENTIFIQUE, Paris (FR); L'UNIVERSITE DE STRASBOURG, Strasbourg (FR)

(72) Inventors: Lorène Gourguillon, Quemper Guezennec (FR); Laetitia Cattuzzato, Castres (FR)

(73) Assignees: BIOTECHMARINE, Quemper Guezennec (FR); SOCIETE D'EXPLOITATION DE PRODUITS POUR LES INDUSTRIES CHIMIQUES SEPPIC, Paris (FR); CENTRE NATIONAL DE LA RECHERCHE SCIENTIFIQUE, Paris (FR); L'UNIVERSITE DE STRASBOURG, Strasbourg (FR)

( * ) Notice: Subject to any disclaimer, the term of this patent is extended or adjusted under 35 U.S.C. 154(b) by 720 days.

(21) Appl. No.: 16/312,718

(22) PCT Filed: Jun. 15, 2017

(86) PCT No.: PCT/EP2017/064685
§ 371 (c)(1),
(2) Date: Dec. 21, 2018

(87) PCT Pub. No.: WO2017/220426
PCT Pub. Date: Dec. 28, 2017

(65) Prior Publication Data
US 2019/0336435 A1    Nov. 7, 2019

(30) Foreign Application Priority Data

Jun. 23, 2016  (FR) ...................................... 1655868

(51) Int. Cl.
*A61K 8/9789* (2017.01)
*A61K 8/34* (2006.01)
*A61Q 19/08* (2006.01)

(52) U.S. Cl.
CPC .............. *A61K 8/9789* (2017.08); *A61K 8/34* (2013.01); *A61Q 19/08* (2013.01)

(58) Field of Classification Search
None
See application file for complete search history.

(56) References Cited

U.S. PATENT DOCUMENTS

| 2006/0134059 A1 | 6/2006 | Dryer et al. |
| 2015/0164813 A1 | 6/2015 | Chen et al. |

FOREIGN PATENT DOCUMENTS

| EP | 0 971 683 A1 | 1/2000 | |
| EP | 1 515 688 B1 | 7/2013 | |
| EP | 2 722 075 A1 | 4/2014 | |
| EP | 2722075 A1 * | 4/2014 | ............. A61Q 19/00 |
| FR | 2 783 169 A1 | 3/2000 | |
| FR | 3 031 040 A1 | 7/2016 | |
| WO | 96/00719 A1 | 1/1996 | |
| WO | 97/17835 A2 | 5/1997 | |
| WO | 98/44902 A1 | 10/1998 | |
| WO | 03/103616 A1 | 12/2003 | |
| WO | 2010/056908 A1 | 5/2010 | |
| WO | 2010/127396 A1 | 11/2010 | |

OTHER PUBLICATIONS

International Search Report for PCT/EP2017/064685 dated Sep. 15, 2017.
FR Search Report issued in FR Patent Application No. 1655868 dated Jan. 20, 2017.
Rathinasabapathi et al., "β-alanine Betaine Synthesis in the Plumbaginaceae. Purification and Characterization of a Trifunctional, S-Adenosyl-L-Methionine-Dependent N-Methyltransferase from Limonium Iatifolium Leaves," Plant Physiology, Jul. 2001, vol. 126, pp. 1241-1249.
Demirovic et al., "Curcumin induces stress response and hormetically modulates wound healing ability of human skin fibroblasts undergoing ageing in vitro," 2011, Biogerontology, Mar. 6, 2011, pp. 437-444.
Baraibar et al., "Oxidative proteome modifications target specific cellular pathways during oxidative stress, cellular senescence and ageing," Experimental Gerontology, 2013, vol. 48, No. 7, pp. 620-625.
Fisher et al., "Molecular mechanisms of photoaging and its prevention by retinoic acid: ultraviolet irradiation induces MAP kinase signal transduction cascades that induce Ap-1-regulated matrix metalloproteinases that degrade human skin in vivo," J. Investig. Dermatol. Symp. Proc., Aug. 1998, vol. 3, No. 1, pp. 61-68.
Jang et al., "Prolonged activation of ERK contributes to the photorejuvenation effect in photodynamic therapy in human dermal fibroblasts," Journal of Investigative Dermatology, 2013, vol. 133, No. 9, pp. 2265-2275.
Rojo et al., "Wound healing properties of nut oil from Pouteria lucuma," Sep. 2010, J. Cosmet. Dermatol., vol. 9, No. 3, pp. 185-195.
Schulze et al., "Stiffening of human skin fibroblasts with age," Clin. Plast. Surg., 2012, vol. 39, No. 1, pp. 9-20.

(Continued)

*Primary Examiner* — Michael Barker
(74) *Attorney, Agent, or Firm* — Nixon & Vanderhye

(57) ABSTRACT

Disclosed are a method for preparing a hydroalcoholic extract obtained from a biomass of the shoots of a plant from the family of Plumbaginaceae, a butanol extract of *Armenia maritima*, a method for the preparation thereof, the use thereof, and compositions containing same.

16 Claims, No Drawings

(56) References Cited

OTHER PUBLICATIONS

Tang et al., "A rice-derived recombinant human lactoferrin stimulates fibroblast proliferation, migration, and sustains cell survival," 2010, Wound Repair Regeneration, vol. 18, pp. 123-131.
Houreld et al., "Low-intensity laser irradiation stimulates wound healing in diabetic wounded fibroblast cells (WS1)," 2010, Diabetes Technology & Therapeutics, vol. 12, No. 12, pp. 971-978.
Kondo et al., "Inhibitory effects of human serum on human fetal skin fibroblast migration: migration-inhibitory activity and substances in serum, and its age-related changes," In Vitro Cell Dev. Biol. Anim., 2000, vol. 36, No. 4, pp. 256-261.
Rathinasabapathi et al., "Osmoprotectant β-alanine betaine synthesis in the Plumbaginaceae: S-adenosyl-I-methionine dependent N-methylation of β-alanine to its betaine is via N-methyl and N,N-dimethyl β-alanines," Physiologia Plantarum, vol. 109, 2000, pp. 225-231.

* cited by examiner

METHOD FOR OBTAINING A DIGLYCOSIDE-ENRICHED *ARMERIA MARITIMA* EXTRACT, AND USE THEREOF IN COSMETICS

A subject of the present invention is a novel plant extract, the process for preparing same and the use thereof as cosmetic active agent, and the cosmetic, pharmaceutical and dermopharmaceutical compositions for topical use comprising same.

Since the human skin is the first thing noticed by others, improving the appearance thereof is a constant preoccupation for humans. The skin reflects either a state of well-being, often associated with youthfulness, or on the contrary a state of fatigue and/or aging. Skin aging is therefore a preoccupation for humans and more particularly for consumers of cosmetic products who seek solutions to alleviate and/or prevent visible signs associated with said aging. This skin aging is observed in different cutaneous tissues and is characterized by metabolic, functional, cellular, architectural, and tissue alterations, leading to visible external effects characterized by the appearance and growth of wrinkles, a dull complexion and/or a lack of uniformity of this complexion (dyschromia) or else the modification of the texture and properties, especially biomechanical properties, of the skin of the human body.

Skin aging results on the one hand from factors unique to each individual (characteristics of the genetic heritage unique to each individual) and on the other hand from environmental factors. Among the environmental factors which may cause skin aging, there is the repeated and prolonged exposure to the sun, and more particularly to ultraviolet radiation, exposure to atmospheric pollution, to cigarette smoke, various oxidative stresses that may result inter alia from the abovementioned factors, and also psychological, emotional and anxiety-related stresses. Repeated and prolonged exposure of the human skin to solar radiation, and more particularly to ultraviolet radiation, leads to a form of aging that is commonly referred to as photoaging. This photoaging is well-documented in the scientific literature: it causes alterations to the skin at various levels, including the most well-known of which, solar elastosis, which is characterized by profound modifications to the architecture and organization of the elastic fibers of the dermis.

The dermis is the main structural cutaneous tissue of the skin. It is a dense, sparsely vascularized connective tissue. It comprises fibroblasts, which are the main cells responsible for the synthesis and maintenance of this tissue. These cells are surrounded by extracellular matrix which is mainly composed of collagen fibers, elastic fibers, glycosaminoglycans such as hyaluronic acid, proteoglycans and structural glycoproteins such as fibronectin. In order to ensure the maintenance and renewal of this tissue, the fibroblasts permanently synthesize these macromolecules and also specific enzymes enabling them to be broken down. Among these enzymes, mention may be made of elastases, enzymes that specifically degrade elastic fibers, and matrix metalloproteases (MMPs), enzymes which degrade the matrix macromolecules such as collagens, proteoglycans and fibronectin. The expression of these enzymes increases with aging (chronological photo- or induced aging, or aging associated with environmental conditions); they promote destructuring of the dermis which is reflected in the formation of wrinkles and the accentuation thereof over time. The class of MMPs contains different enzymes including collagenases (MMP-1, MMP-8 and MMP-13), capable of degrading fibrillar collagens containing triple helices. [G. J. Fisher et al. "*Molecular mechanisms of photoaging and its prevention by retinoic acid: ultraviolet irradiation induces MAP kinase signal transduction cascades that induce Ap-1-regulated matrix metalloproteinases that degrade human skin in vivo.*" J. Investig. Dermatol. Symp. Proc. 1998 August; 3(1):61-8.]

The modifications of the dermis lead to a characteristic appearance of skin altered by photoaging, having very deep and pronounced wrinkles, giving the appearance of leathery skin, that is to say stiff, cracked and brown, and also modifications to the mechanical properties thereof. These modifications are due to the alteration of the dermal extracellular matrix, composed of elastic fibers and collagen fibers, and also to the alteration of cell characteristics. Schulze et al. showed that dermal fibroblasts stiffened with age, influencing cellular functions involving the cytoskeleton, such as contractile, migratory and proliferative properties, which are important for reorganization of the extracellular matrix (Schulze et al., "*Stiffening of human skin fibroblasts with age*"; Clin. Plast. Surg.; 2012; 39(1):9-20).

Reactive oxygen species (known under the acronym "ROS") in excess in human skin (whether by exogenous stimulus or endogenous production) create irreversible bonds with proteins, identified by the term "carbonylated proteins", which then lose their function. A connection has recently been demonstrated between these carbonylated proteins and their impact on key cellular functions such as carbohydrate metabolism, protein maintenance, cell mobility, including migration and protein homeostasis [Baraibar and Friguet, "*Oxidative proteome modifications target specific cellular pathways during oxidative stress, cellular senescence and ageing*"; Exp. Gerontol. 2013; 48(7):620-5].

Studies investigating the effect of human sera, originating from donors of various ages, on the migratory properties of fibroblasts were performed by Kondo et al. [Kondo et al. "*Inhibitory effects of human serum on human fetal skin fibroblast migration: migration-inhibitory activity and substances in serum, and its age-related changes*"; In Vitro Cell Dev. Biol. Anim.; 2000; 36(4):256-61]. The data obtained show that the serum of elderly donors inhibits the migratory properties of fibroblasts, and even those of fetal fibroblasts. This illustrates the importance of the intrinsic factors in the problem of aging of the skin.

The "photodynamic" technique has been described as being particularly suitable for rejuvenating (i.e. reducing the wrinkles and fine lines, pigmentary marks, etc.) "photoexposed" skin, i.e. skin exposed to solar radiation, and more particularly to ultraviolet radiation. The mechanism via which this technique acts has recently been studied, and it appears that its mode of action proceeds especially via an increase in the fibroblast population and also via an increase in the migratory capacity of said fibroblasts [Jang et al., "*Prolonged activation of ERK contributes to the photorejuvenation effect in photodynamic therapy in human dermal fibroblasts*"; JID, 2013; 133(9):2265-75].

These recent studies show that impairment of the migratory properties of fibroblasts contributes to the phenomenon of aging of the skin. These migratory properties are important and described in the context of the process of repair of skin lesions. Dysfunctions of this process in the case of the elderly are widely described, illustrating the importance of this cellular functionality.

As a result, improving the migratory properties of the dermal fibroblasts of human skin and/or increasing the fibroblast population constitute means for preventing and/or treating aging of human bodily skin, and more particularly for preventing and/or treating the visible effects of said aging, for example wrinkles, dull complexion, lack of uniformity of the complexion (dyschromia) and stiffness of the skin, caused by natural aging or by prolonged exposure to sunlight, and more particularly exposure to ultraviolet radiation, or by exposure to oxidative stresses.

Physical processes intended for stimulating the migration of human skin fibroblasts are known, and, among these, mention may be made of low-intensity laser irradiation (exposure to a wavelength of 632.2 nm) more particularly intended for patients suffering from diabetes [Houreld et al. "*Low-intensity laser irradiation stimulates wound healing in diabetic wounded fibroblast cells (WS1)*", 2010, Diabetes Technol Ther, December; 12(12)].

Many pharmaceutical active ingredients also exist, which stimulate fibroblast migration and which are mainly prescribed for the wound healing process. Mention may thus be made of recombinant human lactoferrin produced by transgenic rice plants [Tang et al., "*A rice-derived recombinant human lactoferrin stimulates fibroblast proliferation, migration, and sustains cell survival*", 2010, Wound Repair Regen, January-February 18(1)]. These physical processes and these pharmaceutical active ingredients are generally used for individuals suffering from a pathological condition that impacts the quality of their skin, and are unsuitable for cosmetic uses.

Cosmetic active ingredients also exist which are plant or bacterial extracts and which are described as acting on fibroblast migration. Mention may thus be made of *curcumin* extracts, which stimulate wound healing when used at low doses and act on fibroblast migration at higher doses [Demirovic et al., "*Curcumin induces stress response and hormetically modulates wound healing ability of human skin fibroblasts undergoing ageing in vitro*", 2011, Biogerontology, March 6]; the oil extracted from Pouteria lucuma nuts, characterized by the majority presence of linoleic acid, oleic acid, palmitic acid, stearic acid and γ-linolenic acid, and described as stimulating fibroblast migration and vinculin expression, and being suitable for accelerating skin wound healing [Rojo et al., "*Wound healing properties of nut oil from Pouteria lucuma*", 2010, J. Cosmet. Dermatol., September 9(3)].

The combination of extracts of *Vigna marina, Cocos nucifera, Terminalia catappa* and *Hibiscus tiliaceus* present in cosmetic compositions for treating wounds, improving wound healing and treating age-related skin problems is described in the international patent application published under the number WO 2010/127396 A1.

The international patent application published under the number WO 2010/056908 A1 discloses the use of an extract of Pouteria lucuma and more particularly of the oil contained in their kernel, for improving the migration of human fibroblasts. However, the use of plant and/or bacterial extracts has the drawback of showing unreliable performance over time due to the variability of the content of the starting materials.

Synthetic cosmetic active ingredients also exist, for example peptides, which are described as acting on fibroblast migration. Mention may thus be made of pentapeptides of formula Lys-Thr-Thr-Lys-X in which X represents any natural amino acid but preferentially serine and of which a fatty acid chain (C2 to C22) is grafted onto the N-terminal amine and/or its esterified carboxyl group, described in the French patent application published under the number FR 2 783 169. These pentapeptides are incorporated into cosmetic or pharmaceutical compositions to bring about an increase in the synthesis of collagen and glycosaminoglycans (demonstrated by radioactivity) on skin explants and an increase in the proliferation of normal human fibroblasts in culture, and consequently to improve the appearance of the skin (in the context of its natural aging), the drying out thereof and the wound healing thereof.

The international patent application published under the number WO 97/17835 discloses peptides containing at least one sequence of three amino acids (Lys-Lys-Gly, Gly-His-Lys or Glu-His-Lys) conjugated to a monocarboxylic or dicarboxylic acid, incorporated into cosmetic or pharmaceutical compositions as a wound-healing and antiwrinkle agent, showing an effect on the synthesis of collagen I by fibroblasts.

"*Armeria maritima*" or sea thrift is a herbaceous carpeting plant from 5 to 30 cm in height. Its leaves are planar linear-obtuse and have a single vein. The stems are slightly hairy. The sheath of approximately 10 cm is generally shorter than the flower head, which is dense and broad (approximately 15 cm wide). The flowers are pinkish, occasionally white. The involucre is ferruginous-green, with leaflets over 3 or 4 rows, the outsides being oval, acuminated or mucronated, herbaceous on the reverse and scarious on the edges. The calyx is tubular, as is the pedicel, with ribs as wide as the grooves, with oval lobes split by ridges that are much shorter than they are. In France, this plant grows on lawns and cliff-tops of the Atlantic Coast and the English Channel Coast. It is also found in Western and Northern Europe and Northern Asia. It should also be noted that this plant is often used as an ornamental plant to decorate flower beds.

The genus *Armeria* belongs to the order of the Caryophyllales and more particularly to the Plumbaginaceae family. *Armeria maritima* is a halophilic plant, that is to say capable of growing in a saline environment, like other species of the Plumbaginaceae family such as those belonging to the genus *Limonium*. In order to withstand salt stress, halophytes are able to synthesize osmoprotective metabolites, such as for example glycine betaine, but also metabolites making it possible to protect against the oxidative stress directly associated with salt stress. [Rathinasabapathi, B. et al. "*Osmoprotectant β-alanine betaine synthesis in the Plumbaginaceae: S-adenosyl-1-methionine dependent N-methylation of β-alanine to its betaine is via N-methyl and N,N-dimethyl β-alanines*", Physiol. Plant. 109, 225-231 (2000)].

The European patent application published under the number EP 2 722 075 A1 discloses the use of an aqueous extract of *Armeria maritima* obtained by a process using supercritical carbon dioxide for treating skin inflammation and irritation.

However, it has been observed that certain extracts of this plant, which is rich in flavonoid compounds, were phototoxic.

It is for this reason that the inventors set themselves the task of developing a process for extracting compounds originating from the "*Armeria maritima*" plant which makes it possible to obtain non-phototoxic extracts that can be used in cosmetics.

According to a first aspect, a subject of the invention is a process for preparing an alcohol extract originating from a biomass of aerial parts of a plant of the Plumbaginaceae family (Plumbaginaceae; Interagency Taxonomic Information System (ITIS) Taxonomic serial number: 21324), comprising the following successive steps:

at least one step A) of maceration in an aqueous-alcoholic solution of said aerial parts of said plant of the Plumbaginaceae family, for which the alcohol used is chosen from methanol or ethanol, in order to obtain an aqueous-alcoholic suspension therefrom;

at least one step B) of filtration of said aqueous-alcoholic suspension obtained in step A), in order to separate an aqueous-alcoholic extract from the plant biomass;

a step C) of drying said aqueous-alcoholic extract obtained in step B), in order to obtain a dry residue therefrom;

a step D) of dissolving said dry residue obtained in step C) in water, in order to obtain an aqueous phase $\phi_0$;

at least one first step $E_1$) of liquid-liquid extraction by bringing said aqueous phase $\phi_0$ obtained in step D) into contact with a nonpolar organic solvent, in order to obtain, after separation of the immiscible phases, a new aqueous phase $\phi_1$, at least one second step $E_2$) of liquid-liquid extraction by bringing said aqueous phase $\phi_1$ obtained in step $E_1$) into contact with a polar aprotic organic solvent, in order to obtain, after separation of the immiscible phases, a new aqueous phase $\phi_2$, at least one third step $E_3$) of liquid-liquid extraction by bringing said aqueous phase $\phi_2$ obtained in step $E_2$) into contact with a polar protic organic solvent chosen from alkanols comprising from four to eight carbon atoms, said alkanols previously being saturated with water, or alkanediols comprising from four to eight carbon atoms, said alkanediols previously being saturated with water, in order to obtain, after separation of the immiscible phases, said expected alcoholic extract and a new aqueous phase $\phi_3$.

Step A) of the process as defined above is mainly carried out by preparing a mixture of an aqueous-alcoholic solution predominantly consisting of alcohol, with a sample of the aerial parts of a plant of the Plumbaginaceae family that have been dried then pulverized, then by stirring this mixture at room temperature for several minutes to approximately one hour.

Aerial parts of the plant is intended to mean the leaves, stems and/or flowers of said plant.

At the end of this maceration step, the mixture is filtered according to step B) of the process as defined above, in order to separate the aqueous-alcoholic extract from the plant biomass.

If necessary or if desired, said plant biomass resulting from step B) is subjected to a new step A) of the process as defined above, then the aqueous-alcoholic suspension obtained is filtered according to step B), in order therefrom to separate a new aqueous-alcoholic extract from the resulting plant biomass. This process is, if necessary or if desired, repeated several times in order to exhaust the plant biomass of its compounds of interest. All the successive aqueous-alcoholic extracts thus obtained are subsequently mixed, in order to be used in step C).

According to a preferred aspect of the process as defined above, the alcohol used during step A) is ethanol.

According to another preferred aspect of the process as defined above, the ratio by volume of alcohol to water in the aqueous-alcoholic solution used in step A) is between 60% and 90%.

According to another preferred aspect of the process as defined above, said process also comprises, prior to step A):

a step $A_0$ of harvesting said aerial parts of said plant of the Plumbaginaceae family, in order to obtain a biomass therefrom which is subsequently subjected to step A). In this case, the biomass thus obtained is preferably dried according to a step $A_1$), in order to obtain a dried biomass therefrom, which is subsequently subjected to step A).

According to a preferred aspect of the process as defined above, it also comprises:

a step $A_2$) of grinding said biomass obtained in step $A_0$) or said dried biomass obtained in step $A_1$), in order to obtain said biomass therefrom which is subjected to step A).

According to another particular aspect of the process as defined above, it comprises a step $A_3$) of pulverizing-grinding said ground biomass obtained in step $A_2$), in order to obtain said biomass therefrom which is subjected to step A).

Step C) of the process as defined above is generally carried out using a rotary evaporator until complete dryness is achieved.

According to step D) of the process as defined above, the dry residue obtained at the end of step C) is preferably dissolved in water with demineralized water up to the saturation limit of the dry extract, and aided by ultrasound, in order to improve the yield thereof.

Organic solvent used in steps $E_1$, $E_2$ and $E_3$ of the process as defined above denotes:

as nonpolar organic solvent, especially pentane, cyclopentane, hexane, cyclohexane, benzene, toluene or 1,4-dioxane, as polar aprotic organic solvent, especially dichloromethane, tetrahydrofuran, ethyl acetate or dimethyl sulfoxide; and as polar protic organic solvent, 1-butanol, 2-butanol, 1-pentanol, 1-hexanol, 1,3-propanediol, butylene glycol or 1,4-butanediol, 1,3-butanediol, 1,2-butanediol, 1,2-pentanediol, 1,5-pentanediol, 1,2-hexanediol or 1,6-hexanediol.

According to a particular aspect of the process as defined above, said nonpolar organic solvent used during step $E_1$) is hexane or cyclohexane.

According to another particular aspect of the process as defined above, said polar aprotic organic solvent used during step $E_2$) is dichloromethane or ethyl acetate.

According to another particular aspect of the process as defined above, said step $E_2$) consists of a step $E_{2a}$) of liquid-liquid extraction by bringing said aqueous phase $\phi_1$ obtained in step $E_1$) into contact with the dichloromethane, in order to obtain, after separation of the immiscible phases, a new aqueous phase $\phi_{2a}$, followed by a step $E_{2b}$) of liquid-liquid extraction by bringing said aqueous phase $\phi_{2a}$ obtained in step $E_{2a}$) into contact with the ethyl acetate, in order to obtain, after separation of the immiscible phases, said aqueous phase $\phi_2$.

According to another particular aspect of the process as defined above, said polar protic organic solvent used during step $E_3$) is 1-butanol.

During each of steps $E_1$), $E_2$) and $E_3$) of the process as defined above, the ratio by volume of organic solvent to aqueous phase is generally less than or equal to 1.

According to another particular aspect of the process as defined above, during steps $E_1$), $E_2$) and $E_3$), the ratio by volume of organic solvent to, respectively, the aqueous phases $\phi_0$, $\phi_1$ and $\phi_2$, is between ½ and 1/1.

A subject of the invention is more particularly the process as defined above, wherein said plant of the Plumbaginaceae family belongs to the genus *Armeria* Willd. (ITIS Taxonomic serial number: 21325) and most particularly wherein said plant belonging to the genus *Armeria* Willd, is from the species *Armeria maritima* (ITIS Taxonomic serial number: 21326).

Another subject of the invention is the process as defined above, also comprising:

a step F) of evaporation of the alkanol or of the alkanediol of the alcoholic extract obtained in step $E_3$), in order to obtain a dry extract therefrom.

According to a most particular aspect, a subject of the invention is a process as defined above, for preparing a butanolic extract originating from a biomass of aerial parts of *Armeria maritima*, comprising the following successive steps:

a step $A_0$ of harvesting said aerial parts of *Armeria maritima*, in order to obtain therefrom harvested material of said aerial parts;

a step $A_1$) of drying said harvested material obtained in step $A_0$)

a step $A_2$) of grinding said harvested material dried in step $A_1$), in order to obtain a ground material of said dried harvested material;

if necessary, or if desired, a step $A_1$) of pulverizing the ground material obtained in step $A_2$), in order to obtain a powder of said dried harvested material;

at least one step A) of maceration, in an aqueous-ethanolic solution having a ratio by volume of ethanol/water equal to 80/20, of said powder obtained in step $A_3$, in order to obtain an aqueous-ethanolic suspension therefrom;

at least one step B) of filtration of said suspension obtained in step A), in order to separate an aqueous-ethanolic extract therefrom;

a step C) of drying said aqueous-ethanolic extract obtained in step B), in order to obtain a dry residue therefrom;

a step D) of dissolving said dry residue obtained in step C) in water, in order to obtain an aqueous phase $\phi_0$, at least one step $E_1$) of liquid-liquid extraction, by bringing said aqueous phase $\phi_0$ obtained in step D) into contact with cyclohexane at a ratio by volume of cyclohexane/aqueous phase $\phi_0$ equal to $\frac{2}{3}$, in order to obtain, after separation of the immiscible phases, a new aqueous phase $\phi_1$, at least one step $E_{2a}$) of liquid-liquid extraction by bringing said aqueous phase $\phi_1$ obtained in step $E_1$) into contact with dichloromethane at a ratio by volume of dichloromethane/aqueous phase $\phi_1$ equal to $\frac{2}{3}$, in order to obtain, after separation of the immiscible phases, a new aqueous phase $\phi_{2a}$, at least one step $E_{2b}$) of liquid-liquid extraction by bringing said aqueous phase $\phi_{2a}$ obtained in step $E_2$) into contact with ethyl acetate at a ratio by volume of ethyl acetate/aqueous phase $\phi_{2a}$ equal to $\frac{2}{3}$, in order to obtain, after separation of the immiscible phases, a new aqueous phase $\phi_{2b}$, at least one step $E_3$) of liquid-liquid extraction by bringing said aqueous phase $\phi_{2b}$ obtained in step $E_{2b}$) into contact with 1-butanol saturated with water at a ratio by volume of 1-butanol/aqueous phase $\phi_2$ equal to $\frac{2}{3}$, in order to obtain, after separation of the immiscible phases, said expected butanolic extract and a new aqueous phase $\phi_3$.

Another subject of the invention is a butanolic extract of a biomass of aerial parts of *Armeria maritima*, obtained by the process as defined above.

Another subject of the invention is the use of an alcoholic extract originating from a biomass of aerial parts of a plant of the Plumbaginaceae family obtained by the process as defined above or of the dry extract obtained by evaporation according to step F) of the process as defined above, or of the butanolic extract of a biomass of aerial parts of *Armeria maritima* as defined above, as cosmetic anti-aging active agent.

Another subject of the invention is a cosmetic composition ($C_1$) for topical use, comprising at least one cosmetically acceptable excipient and either an effective amount of the alcoholic extract originating from a biomass of aerial parts of a plant of the Plumbaginaceae family obtained by the process as defined above, or an effective amount of the dry extract obtained by evaporation according to step F) of the process as defined above; and more particularly a cosmetic composition ($C_1$) for topical use, comprising at least one cosmetically acceptable excipient and an effective amount of the butanolic extract as defined above.

According to the invention, said composition ($C_1$) is generally spread on the surface of the skin to be treated, then the skin is massaged for a few moments.

The expression "for topical use" used in the definition of the composition ($C_1$) that is a subject of the present invention means that said composition ($C_1$) is used by application to the skin, whether this is direct application or indirect application when said composition ($C_1$) according to the invention is impregnated on a support intended to be placed in contact with the skin (paper, wipe, textile, transdermal device, etc.).

The expression "cosmetically acceptable" used in the definition of the composition ($C_1$) that is a subject of the present invention means, according to the European Economic Community Council directive No. 76/768/EEC of Jul. 27, 1976 amended by directive No. 93/35/EEC of Jun. 14, 1993, that said composition comprises any substance or preparation intended to be placed in contact with the various parts of the human body (epidermis, pilous and hair system, nails, lips and genital organs) or with the teeth and the oral mucosae for the purpose, exclusively and mainly, of cleansing them, fragrancing them, modifying their appearance and/or correcting their body odors and/or protecting them or keeping them in good condition.

For the purposes of the present invention, "cosmetic anti-aging active agent" is intended to mean a chemical substance or a chemical composition or an extract originating from a plant biomass, the property or technical function of which consists in preventing or slowing the appearance of the signs of aging of human skin or lips, or else eliminating said signs.

For the purposes of the invention, "signs of aging of human skin or lips" is intended to mean any modifications to the outward appearance of the skin or the lips that are due to aging, whether chronobiological and/or photo-induced and/or resulting from exposure to environmental stresses (atmospheric pollution, contact with dangerous substances), such as wrinkles and fine lines, impairment of the microrelief, lack of elasticity and/or tonicity of the skin, lack of density and/or firmness of human skin or lips, and also any internal modifications to the skin which are not systematically reflected by a modified outward appearance, for instance any internal degradation of the skin following exposure to ultraviolet radiation.

Effective amount of the aqueous-alcoholic extract originating from a biomass of aerial parts of a plant of the Plumbaginaceae family as defined above is intended to mean, per 100% of the weight of said composition ($C_1$), the amount of between 0.1 and 5% by weight, more particularly between 0.1 and 3% by weight and even more particularly between 0.5 and 2% by weight of said alcoholic extract originating from a biomass of aerial parts of a plant of the Plumbaginaceae family.

The composition ($C_1$) that is a subject of the present invention is generally in the form of an aqueous or aqueous-alcoholic or aqueous-glycolic solution, in the form of a suspension, of an emulsion, of a microemulsion or of a nanoemulsion, whether of the water-in-oil, oil-in-water, water-in-oil-in-water or oil-in-water-in-oil type, or in the form of a powder.

The composition ($C_1$) that is a subject of the present invention may be packaged in a bottle, in a device of pump-bottle type, in pressurized form in an aerosol device, in a device equipped with an openwork wall such as a grate or in a device equipped with a ball applicator (roll-on).

Generally speaking, the aqueous-alcoholic extract originating from a biomass of aerial parts of a plant of the Plumbaginaceae family that is a subject of the present invention is combined with chemical additives usually used in the field of formulations for topical use, such as foaming and/or detergent surfactants, thickening and/or gelling surfactants, thickening and/or gelling agents, stabilizers, film-forming compounds, solvents and co-solvents, hydrotropic agents, spring or mineral waters, plasticizers, emulsifiers and co-emulsifiers, opacifiers, nacreous agents, overfatting agents, sequestrants, chelating agents, oils, waxes, antioxidants, fragrances, essential oils, preserving agents, conditioning agents, deodorizers, bleaching agents intended for bleaching skin and bodily hairs, active ingredients intended for providing a treating and/or protective action on the skin or hair, sunscreens, mineral fillers or pigments, particles affording a visual effect or intended for encapsulating active agents, exfoliant particles, texturing agents, optical brighteners and insect repellents.

As examples of foaming and/or detergent surfactants that may be combined with the aqueous-alcoholic extract originating from a biomass of aerial parts of a plant of the Plumbaginaceae family in the composition ($C_1$), mention may be made of anionic, cationic, amphoteric or nonionic foaming and/or detergent surfactants.

Among the foaming and/or detergent anionic surfactants, mention may be made of salts of alkali metals, of alkaline-earth metals, of ammonium, of amines, or of amino alcohols of alkyl ether sulfates, of alkyl sulfates, of alkylamido ether sulfates, of alkylaryl polyether sulfates, of monoglyceride sulfates, of alpha-olefin sulfonates, of paraffin sulfonates, of alkyl phosphates, of alkyl ether phosphates, of alkylsulfonates, of alkylamide sulfonates, of alkylarylsulfonates, of alkyl carboxylates, of alkylsulfosuccinates, of alkyl ether sulfosuccinates, of alkylamide sulfosuccinates, of alkylsulfoacetates, of alkylsarcosinates, of acylisethionates, of N-acyltaurates, of acyllactylates, of N-acylamino acid derivatives, of N-acyl peptide derivatives, of N-acyl protein derivatives or of N-acyl fatty acid derivatives.

Among the foaming and/or detergent amphoteric surfactants, mention may be made of alkylbetaines, alkylamidobetaines, sultaines, alkylamidoalkylsulfobetaines, imidazoline derivatives, phosphobetaines, amphopolyacetates and amphopropionates.

Among the foaming and/or detergent cationic surfactants, mention may be made particularly of quaternary ammonium derivatives.

Among the foaming and/or detergent nonionic surfactants, mention may be made more particularly of alkylpolyglycosides bearing a linear or branched, saturated or unsaturated aliphatic radical and comprising from 8 to 16 carbon atoms, such as octyl polyglucoside, decyl polyglucoside, undecylenyl polyglucoside, dodecyl polyglucoside, tetradecyl polyglucoside, hexadecyl polyglucoside, 1,12-dodecanediyl polyglucoside; ethoxylated hydrogenated castor oil derivatives, such as the product sold under the INCI name PEG-40 hydrogenated castor oil; polysorbates such as Polysorbate 20, Polysorbate 40, Polysorbate 60, Polysorbate 70, Polysorbate 80 or Polysorbate 85; coconut amides; N-alkylamines.

As examples of thickening and/or gelling surfactants that may be combined with the aqueous-alcoholic extract originating from a biomass of aerial parts of a plant of the Plumbaginaceae family in the composition ($C_1$), mention may be made of optionally alkoxylated alkylpolyglycoside fatty esters, for instance ethoxylated methylpolyglucoside esters such as PEG 120 methyl glucose trioleate and PEG 120 methyl glucose dioleate sold, respectively, under the names Glucamate™ LT and Glumate™ DOE120, alkoxylated fatty esters such as PEG 150 pentaerythrityl tetrastearate sold under the name Crothix™ DS53, or PEG 55 propylene glycol oleate sold under the name Antil™ 141; fatty-chain polyalkylene glycol carbamates such as PPG-14 laureth isophoryl dicarbamate sold under the name Elfacos™ T211, PPG-14 palmeth-60 hexyl dicarbamate sold under the name Elfacos™ GT2125.

As examples of thickeners and/or gelling agents that may be combined with the aqueous-alcoholic extract originating from a biomass of aerial parts of a plant of the Plumbaginaceae family in the composition ($C_1$), mention may be made of polymers of linear, branched or crosslinked polyelectrolyte type, for instance the partially or totally salified acrylic acid homopolymer, the partially or totally salified methacrylic acid homopolymer, the partially or totally salified 2-methyl[(1-oxo-2-propenyl)amino]-1-propanesulfonic acid (AMPS) homopolymer, copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris(hydroxymethyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or of methacrylic acid and of alkyl acrylates in which the carbon-based chain comprises between 4 and 30 carbon atoms and more particularly between 10 and 30 carbon atoms, copolymers of AMPS and of alkyl acrylates in which the carbon-based chain comprises between 4 and 30 carbon atoms and more particularly between 10 and 30 carbon atoms, linear, branched or crosslinked terpolymers of at least one monomer bearing a free, partially salified or totally salified strong acid function, with at least one neutral monomer, and at least one monomer of formula (VIII):

$$CH_2=C(R'_3)-C(=O)-[CH_2-CH_2-O]_n-R'_4 \qquad (VIII)$$

in which $R'_3$ represents a hydrogen atom or a methyl radical, $R'_4$ represents a linear or branched alkyl radical comprising from 8 to 30 carbon atoms and n represents a number greater than or equal to 1 and less than or equal to 50.

The polymers of linear, branched or crosslinked polyelectrolyte type that may be combined with the aqueous-alcoholic extract originating from a biomass of aerial parts of a plant of the Plumbaginaceae family in the composition ($C_1$) may be in the form of a solution, an aqueous suspension, a water-in-oil emulsion, an oil-in-water emulsion or a powder. The polymers of linear, branched or crosslinked polyelectrolyte type that may be combined with the aqueous-alcoholic extract originating from a biomass of aerial parts of a plant of the Plumbaginaceae family in the composition ($C_1$) may be selected from the products sold under the names Simulgel™ EG, Simulgel™ EPG, Sepigel™ 305, Simulgel™ 600, Simulgel™ NS, Simulgel™ INS 100, Simulgel™ FL, Simulgel™ A, Simulgel™ SMS 88, Sepinov™ EMT 10, Sepiplus™ 400, Sepiplus™ 265, Sepiplus™ S, Sepimax™ Zen, Aristoflex™ AVC, Aristoflex™ AVS, Novemer™ EC-1, Novemer™ EC 2, Aristoflex™ HMB, Cosmedia™ SP, Flocare™ ET 25, Flocare™ ET 75, Flocare™ ET 26, Flocare™ ET 30, Flocare™ ET 58, Flocare™ PSD 30, Viscolam™ AT 64 and Viscolam™ AT 100.

As examples of thickeners and/or gelling agents that may be combined with the aqueous-alcoholic extract originating from a biomass of aerial parts of a plant of the Plumbaginaceae family in the composition ($C_1$), mention may be made of polysaccharides constituted solely of saccharides, for instance glucans or glucose homopolymers, glucomannoglucans, xyloglycans, galactomannans in which the degree of substitution (DS) of the D-galactose units on the main D-mannose chain is between 0 and 1, and more particularly between 1 and 0.25, such as galactomannans originating from *cassia* gum (DS=⅕), from locust bean gum (DS=¼), from tara gum (DS=⅓), from guar gum (DS=½) and from fenugreek gum (DS=1).

As examples of thickeners and/or gelling agents that may be combined with the aqueous-alcoholic extract originating from a biomass of aerial parts of a plant of the Plumbaginaceae family in the composition ($C_1$), mention may be made of polysaccharides constituted of saccharide derivatives, such as galactan sulfates and more particularly carrageenans and agar, uronans and more particularly algins, alginates and pectins, heteropolymers of saccharides and of uronic acids and more particularly xanthan gum, gellan gum, gum arabic and karaya gum exudates, and glucosaminoglycans.

As examples of thickeners and/or gelling agents that may be combined with the aqueous-alcoholic extract originating from a biomass of aerial parts of a plant of the Plumbaginaceae family in the composition ($C_1$), mention may be made of cellulose, cellulose derivatives such as methylcellulose, ethylcellulose, hydroxypropylcellulose, silicates, starch, hydrophilic starch derivatives and polyurethanes.

As examples of stabilizers that may be combined with the aqueous-alcoholic extract originating from a biomass of aerial parts of a plant of the Plumbaginaceae family in the composition ($C_1$), mention may be made of microcrystalline waxes, and more particularly ozokerite, mineral salts such as sodium chloride or magnesium chloride, and silicone polymers such as polysiloxane polyalkyl polyether copolymers.

As examples of solvents that may be combined with the aqueous-alcoholic extract originating from a biomass of aerial parts of a plant of the Plumbaginaceae family in the composition ($C_1$), mention may be made of water, organic solvents such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols such as ethanol, isopropanol or butanol, and mixtures of water and of said organic solvents.

As examples of spring or mineral waters that may be combined with the aqueous-alcoholic extract originating from a biomass of aerial parts of a plant of the Plumbaginaceae family in the composition ($C_1$), mention may be made of spring or mineral waters with a mineralization of at least 300 mg/l, in particular Avéne water, Vittel water, Vichy basin water, Uriage water, La Roche-Posay water, La Bourboule water, Enghien-les-Bains water, Saint Gervais-les-Bains water, Néris-les-Bains water, Allevard-les-Bains water, Digne water, Maiziéres water, Neyrac-les-Bains water, Lons-le-Saunier water, Rochefort water, Saint Christau water, Les Fumades water and Tercis-les-Bains water.

As examples of hydrotropic agents that may be combined with the aqueous-alcoholic extract originating from a biomass of aerial parts of a plant of the Plumbaginaceae family in the composition ($C_1$), mention may be made of xylene sulfonates, cumene sulfonates, hexyl polyglucoside, (2-ethylhexyl) polyglucoside and n-heptyl polyglucoside.

As examples of emulsifying surfactants that may be combined with the aqueous-alcoholic extract originating from a biomass of aerial parts of a plant of the Plumbaginaceae family in the composition ($C_1$), mention may be made of nonionic surfactants, anionic surfactants and cationic surfactants.

As examples of emulsifying nonionic surfactants that may be combined with the aqueous-alcoholic extract originating from a biomass of aerial parts of a plant of the Plumbaginaceae family in the composition ($C_1$), mention may be made of fatty acid esters of sorbitol, for example the products sold under the names Montane™ 40 and Montane™ 60, Montane™ 70, Montane™ 80 and Montane™ 85; compositions comprising glyceryl stearate and stearic acid ethoxylated between 5 mol and 150 mol of ethylene oxide, for example the composition comprising stearic acid ethoxylated with 135 mol of ethylene oxide and glyceryl stearate sold under the name Simulsol™ 165; mannitan esters; ethoxylated mannitan esters; sucrose esters; methylglucoside esters; alkylpolyglycosides comprising a linear or branched, saturated or unsaturated aliphatic radical, and comprising from 14 to 36 carbon atoms, such as tetradecyl polyglucoside, hexadecyl polyglucoside, octadecyl polyglucoside, hexadecyl polyxyloside, octadecyl polyxyloside, eicosyl polyglucoside, dodecosyl polyglucoside, 2-octyldodecyl polyxyloside, 12-hydroxystearyl polyglucoside; compositions of linear or branched, saturated or unsaturated fatty alcohols, comprising from 14 to 36 carbon atoms, and of alkyl polyglucosides such as those described above, for example the compositions sold under the trade names Montanov™68, Montanov™ 14, Montanov™82, Montanov™202, Montanov™S, Montanov™WO18, Montanov™L, Fluidanov™20X and Easynov™.

As examples of anionic surfactants that may be combined with the aqueous-alcoholic extract originating from a biomass of aerial parts of a plant of the Plumbaginaceae family in the composition ($C_1$), mention may be made of glyceryl stearate citrate, cetearyl sulfate, soaps such as sodium stearate or triethanolammonium stearate, salified N-acylamino acid derivatives, for example stearoyl glutamate.

As examples of emulsifying cationic surfactants that may be combined with the aqueous-alcoholic extract originating from a biomass of aerial parts of a plant of the Plumbaginaceae family in the composition ($C_1$), mention may be made of aminoxides, quaternium-82 and the surfactants described in patent application WO 96/00719 and mainly those whose fatty chain comprises at least 16 carbon atoms.

As examples of opacifiers and/or nacreous agents that may be combined with the aqueous-alcoholic extract originating from a biomass of aerial parts of a plant of the Plumbaginaceae family in the composition ($C_1$), mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, and fatty alcohols comprising from 12 to 22 carbon atoms.

As examples of texturing agents that may be combined with the aqueous-alcoholic extract originating from a biomass of aerial parts of a plant of the Plumbaginaceae family in the composition ($C_1$), mention may be made of N-acylamino acid derivatives, such as lauroyl lysine sold under the name Aminohope™ LL, octenyl starch succinate sold under the name DryFlo™, myristyl polyglucoside sold under the name Montanov™ 14, cellulose fibers, cotton fibers, chitosan fibers, talc, sericite and mica.

As examples of deodorants that may be combined with the aqueous-alcoholic extract originating from a biomass of aerial parts of a plant of the Plumbaginaceae family in the composition ($C_1$), mention may be made of alkaline silicates, zinc salts such as zinc sulfate, zinc gluconate, zinc chloride or zinc lactate; quaternary ammonium salts such as cetyltrimethylammonium salts, and cetylpyridinium salts; glycerol derivatives such as glyceryl caprate, glyceryl caprylate, polyglyceryl caprate; 1,2-decanediol, 1,3-propanediol, salicylic acid; sodium bicarbonate; cyclodextrins; metal zeolites; Triclosan™; aluminum hydrobromide, aluminum hydrochlorides, aluminum chloride, aluminum sulfate, aluminum zirconium hydrochlorides, aluminum zirconium trihydrochloride, aluminum zirconium tetrahydrochloride, aluminum zirconium pentahydrochloride, aluminum zirconium octahydrochloride, aluminum sulfate, sodium aluminum lactate, complexes of aluminum hydrochloride and glycol, such as the complex of aluminum hydrochloride and of propylene glycol, the complex of aluminum dihydrochloride and of propylene glycol, the complex of aluminum sesquihydrochloride and of propylene glycol, the complex of aluminum hydrochloride and of polyethylene glycol, the complex of aluminum dihydrochloride and of polyethylene glycol, the complex of aluminum sesquihydrochloride and of polyethylene glycol.

As examples of oils that may be combined with the aqueous-alcoholic extract originating from a biomass of aerial parts of a plant of the Plumbaginaceae family in the composition ($C_1$), mention may be made of mineral oils such as liquid paraffin, liquid petroleum jelly, isoparaffins or white mineral oils; oils of animal origin, such as squalene or squalane; plant oils, such as phytosqualane, sweet almond oil, coconut oil, castor oil, jojoba oil, olive oil, rapeseed oil, groundnut oil, sunflower oil, wheatgerm oil, corn germ oil, soybean oil, cotton oil, alfalfa oil, poppy oil, pumpkin oil, evening primrose oil, millet oil, barley oil, rye oil, safflower oil, candlenut oil, passion flower oil, hazelnut oil, palm oil, shea butter, apricot kernel oil, beauty-leaf oil, sysymbrium oil, avocado oil, calendula oil, oils derived from flowers or vegetables, ethoxylated plant oils; synthetic oils, for instance fatty acid esters such as butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, lanolic acid-based esters, such as isopropyl lanolate, isocetyl lanolate, fatty acid monoglycerides, diglycerides and triglycerides, for instance glyceryl triheptanoate, alkylbenzoates, hydrogenated oils, poly(alpha-olefins), polyolefins such as poly (isobutane), synthetic isoalkanes such as isohexadecane, isododecane, perfluoro oils; silicone oils such as dimethylpolysiloxanes, methylphenylpolysiloxanes, silicones modified with amines, silicones modified with fatty acids, silicones modified with alcohols, silicones modified with alcohols and fatty acids, silicones modified with polyether groups, modified epoxy silicones, silicones modified with fluoro groups, cyclic silicones and silicones modified with alkyl groups. In the present application, the term "oils" is intended to mean compounds and/or mixtures of compounds that are insoluble in water, which have a liquid appearance at a temperature of 25° C.

As examples of waxes that may be combined with the aqueous-alcoholic extract originating from a biomass of aerial parts of a plant of the Plumbaginaceae family in the composition ($C_1$), mention may be made of beeswax, carnauba wax, candelilla wax, ouricury wax, Japan wax, cork fiber wax, sugar cane wax, paraffin waxes, lignite waxes, microcrystalline waxes, lanolin wax; ozokerite; polyethylene wax; silicone waxes; plant waxes; fatty alcohols and fatty acids that are solid at room temperature; glycerides that are solid at room temperature. In the present application, the term "waxes" is intended to mean water-insoluble compounds and/or mixtures of compounds, which have a solid appearance at a temperature of greater than or equal to 45° C.

As examples of active ingredients that may be combined with the aqueous-alcoholic extract originating from a biomass of aerial parts of a plant of the Plumbaginaceae family in the composition ($C_1$), mention may be made of vitamins and derivatives thereof, especially esters thereof, such as retinol (vitamin A) and esters thereof (for example retinyl palmitate), ascorbic acid (vitamin C) and esters thereof, sugar derivatives of ascorbic acid (such as ascorbyl glucoside), tocopherol (vitamin E) and esters thereof (such as tocopheryl acetate), vitamin B3 or B10 (niacinamide and derivatives thereof); compounds which show lightening or depigmenting action on the skin, such as w-undecelynoyl phenylalanine sold under the name Sepiwhite™ MSH, Sepicalm™ VG, the glyceryl monoester and/or diester of w-undecelynoyl phenylalanine, w-undecelynoyl dipeptides, arbutin, kojic acid, hydroquinone; compounds showing calmative action, especially Sepicalm™ S, allantoin and bisabolol; antiinflammatory agents; compounds showing moisturizing action, such as urea, hydroxyureas, glycerol, polyglycerols, glycerol glucoside, diglycerol glucoside, polyglyceryl glucosides, xylityl glucoside; the composition sold under the trade name Aquaxyl™, the composition sold under the trade name Pro-Xylane™, C-glycoside derivatives and more particularly C-glucoside or C-xyloside derivatives; polyphenol-rich plant extracts such as grape extracts, pine extracts, vine extracts and olive extracts; compounds showing slimming or lipolytic action such as caffeine or derivatives thereof, Adiposlim™ Adipoless™, fucoxanthin; N-acyl proteins; N-acyl peptides such as Matrixyl™; N-acylamino acids; N-acyl partial protein hydrolysates; amino acids; peptides; total protein hydrolyzates; soybean extracts, for example Raffermine™ wheat extracts, for example Tensine™ or Gliadine™; plant extracts, such as tannin-rich plant extracts, isoflavone-rich plant extracts or terpene-rich plant extracts; freshwater or marine water algal extracts; marine plant extracts; marine extracts in general such as corals; essential waxes; bacterial extracts; ceramides; phospholipids; compounds showing antimicrobial action or purifying action, such as Lipacide™ C8G, Lipacide™ UG, Sepicontrol™ A5, Fluidipure™ 8 G, Octopirox™ or Sensiva™ SC50, compounds showing an energizing or stimulating property such as Physiogenyl™, panthenol and derivatives thereof such as Sepicap™ MP; antiaging active agents such as Sepilift™ DPHP, Lipacide™ PVB, Sepivinol™ Sepivital™, Manoliva™, Phyto-Age™, Timecode™; Survicode™; anti-photoaging active agents; active agents for protecting the integrity of the dermo-epidermal junction; active agents for increasing the synthesis of components of the extracellular matrix, such as collagen, elastins and glycosaminoglycans; active agents acting favorably on chemical cellular communication, such as cytokines, or physical cellular communication, such as integrins; active agents creating a sensation of "heating" on the skin, such as skin microcirculation activators (such as nicotinic acid derivatives) or products that create a sensation of "coolness" on the skin (such as menthol and derivatives thereof); active agents which improve the skin microcirculation, for example venotonic agents; draining active agents; decongestant active agents such as *Ginkgo biloba*, ivy, common horse chestnut, bamboo, ruscus, butcher's-broom, *Centella asiatica*, fucus, rosemary or willow extracts; skin tanning or bronzing agents, for instance dihydroxyacetone (DHA), erythrulose, mesotartaric aldehyde, glutaraldehyde, glyceraldehyde, alloxan, ninhydrin, plant extracts, for example extracts of red woods of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in European patent application EP 0 971 683 agents known for their action of promoting and/or accelerating tanning and/or bronzing of human skin, and/or for their action of coloring human skin, for example carotenoids (and more particularly beta carotene and gamma carotene), the product sold under the trade name "Carrot oil" (INCI name: *Daucus carotta, Helianthes annuus* Sunflower oil) by Provital, which contains carotenoids, vitamin E and vitamin K; tyrosine and/or derivatives thereof, known for their effect on the acceleration of the tanning of human skin in combination with exposure to ultraviolet radiation, for example the product sold under the trade name "SunTan Accelerator™" by Provital which contains tyrosine and riboflavins (vitamin B), the complex of tyrosine and tyrosinase sold under the trade name "Zymo Tan Complex" by Zymo Line, the product sold under the trade name Malan® Bronze™ (INCI name: Acetyl Tyrosine, Monk's pepper extract (Vitex Agnus-castus)) by Mibelle which contains acetyl tyrosine, the product sold under the trade name Unipertan VEG-24/242/2002 (INCI name: butylene glycol and Acetyl Tyrosine and hydrolyzed vegetable protein and Adenosine triphosphate) by UNIPEX, the product sold under the trade name "Try-Excell™" (INCI name: Oleoyl Tyrosine and *Luffa Cylindrica* (Seed) Oil and Oleic acid) by Sederma which contains extracts of marrow seeds (or loofah oil), the product sold under the trade name "Actibronze™" (INCI name: hydrolyzed wheat protein and acetyl tyrosine and copper gluconate) by Alban Muller, the product sold under the trade name Tyrostan™ (INCI name: potassium caproyl tyrosine) by Synerga, the product sold under the trade name Tyrosinol (INCI name: Sorbitan Isostearate, glyceryl oleate, caproyl Tyrosine) by Synerga, the product sold under the trade name InstaBronze™ (INCI name: Dihydroxyacetone and acetyl tyrosine and copper gluconate) by Alban Muller, the product sold under the trade name Tyrosilane (INCI name: methylsilanol and acetyl tyrosine) by Exymol; peptides known for their effect of activation of melanogenesis, for example the product sold under the trade name Bronzing SF Peptide powder (INCI name: Dextran and Octapeptide-5) by Infinitec Activos, the product sold under the trade name Melitane (INCI name: Glycerin and Aqua and Dextran and Acetyl hexapeptide-1) comprising acetyl hexapeptide-1, known for alpha-MSH agonist action, the product sold under the trade name Melatimes Solutions™ (INCI name: Butylene glycol, Palmitoyl Tripeptide-40) by LIPOTEC, sugars and sugar derivatives, for example the product sold under the trade name Tanositol™ (INCI name: inositol) by Provital, the product sold under the trade name Thalitan™ (or Phycosaccharide™ AG) by CODIF international (INCI name: Aqua and hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, Mucuna Pruriens Seed extract) by Alban Muller, flavonoid-rich compounds, for example the product sold under the trade name "Biotanning" (INCI name: Hydrolyzed *Citrus aurantium dulcis* fruit extract) by Silab and known to be rich in lemon flavonoids (of hesperidin type); agents intended for the treatment of head and/or body hair, for example agents for protecting the melanocytes of the hair follicle, intended to protect said melanocytes from cytotoxic agents responsible for senescence and/or apoptosis of said melanocytes, such as mimetics of DOP-Achrome tautomerase activity, chosen from those described in the European patent application published under EP 1 515 688 A2, synthetic SOD mimetic molecules, for example manganese complexes, antioxidant compounds, for example cyclodextrin derivatives, silica-containing derivatives of ascorbic acid, lysine or arginine pyrrolidone carboxylate, combinations of monoesters and diesters of cinnamic acid and vitamin C, and more generally those mentioned in the European patent application published under the number EP 1 515 688 A2.

As examples of antioxidants that may be combined with the aqueous-alcoholic extract originating from a biomass of aerial parts of a plant of the Plumbaginaceae family in the composition ($C_1$), mention may be made of EDTA and salts thereof, citric acid, tartaric acid, oxalic acid, BHA (butyl hydroxyanisole), BHT (butyl hydroxytoluene), tocopherol derivatives such as tocopheryl acetate, mixtures of antioxidant compounds such as Dissolvine™ GL 47S sold by Akzo Nobel under the INCI name: Tetrasodium Glutamate Diacetate.

As examples of sunscreens that may be combined with the aqueous-alcoholic extract originating from a biomass of aerial parts of a plant of the Plumbaginaceae family in the composition ($C_1$), mention may be made of all those featured in the cosmetic directive 76/768/EEC amended annex VII.

Among the organic sunscreens that may be combined with the aqueous-alcoholic extract originating from a biomass of aerial parts of a plant of the Plumbaginaceae family in the composition ($C_1$), mention may be made of the family of benzoic acid derivatives for instance para-aminobenzoic acids (PABA), especially monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA and butyl esters of N,N-dimethyl PABA; the family of anthranilic acid derivatives, for instance homomenthyl-N-acetyl anthranilate; the family of salicylic acid derivatives, for instance amyl salicylate, homomenthyl salicylate, ethylhexyl salicylate, phenyl salicylate, benzyl salicylate and p-isopropanolphenyl salicylate; the family of cinnamic acid derivatives, for instance ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyl cinnamate, p-methoxy-2-ethylhexyl cinnamate, p-methoxy-2-ethoxyethyl cinnamate, p-methoxycyclohexyl cinnamate, ethyl-α-cyano-β-phenyl cinnamate, 2-ethylhexyl-α-cyano-β-phenyl cinnamate or glyceryl di-para-methoxy-mono-2-ethylhexanoyl cinnamate; the family of benzophenone derivatives, for instance 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, for instance 2-phenylbenzimidazole-5-sulfonic acid and salts thereof; the family of triazine derivatives, for instance hydroxyphenyltriazine, (ethylhexyloxyhydroxyphenyl)(4-methoxyphenyl) triazine, 2,4,6-trianillino(p-carbo-2'-ethylhexyl-1'-oxy)-1,3,5-triazine, 4,4-((6-(((1,1-dimethylethyl)amino)carbonyl) phenyl)amino)-1,3,5-triazine-2,4-diyldiimino)bis-(2-ethyl hexyl) benzoate, 2-phenyl-5-methylbenzoxazole, 2,2'-hydroxy-5'-methylphenylbenzotriazole, 2-(2'-hydroxy-5'-t-octylphenyl)benzotriazole, 2-(2'-hydroxy-5'-methylphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenylacrylate derivatives, for instance 2-ethylhexyl-2-cyano-3,3-diphenyl-2-propenoate, ethyl-2-cyano-3,3-diphenyl-2-propenoate; the family of polysiloxanes, for instance benzylidene siloxane malonate.

Among the mineral sunscreens, also known as "mineral sunblocks", that may be combined with the aqueous-alcoholic extract originating from a biomass of aerial parts of a plant of the Plumbaginaceae family in the composition ($C_1$), mention may be made of titanium oxides, zinc oxides, cerium oxide, zirconium oxide, yellow, red or black iron oxides, and chromium oxides. These mineral sunblocks may or may not be micronized, may or may not have undergone surface treatments and may be optionally in the form of aqueous or oily predispersions.

The examples that follow illustrate the invention without, however, limiting it.

Preparation of a Butanolic Extract of *Armeria maritima* (Extract AmB)

The butanolic extract of *Armeria maritima* is prepared by carrying out the following successive steps:

1)—Harvest

The aerial parts of the flowering plant are harvested.

2)—Drying

The harvested material is dried in order to avoid degradation thereof and to facilitate preservation thereof during transport.

3)—Grinding

The aerial parts (stems, leaves, flowers) are finely ground in order to increase the extraction yield.

4)—Aqueous-ethanolic maceration

A plant/solvent mixture (ethanol/water 80/20) is subjected to stirring using a paddle. The extract is filtered and the pomace is re-extracted (two more times) in order to exhaust the plant material and thereby increase the extraction yield. The three aqueous-alcoholic extracts are brought together. (Extract AmE)

5)—Drying of the aqueous-ethanolic extract

The aqueous-alcoholic extract obtained above is evaporated to dryness using a rotary evaporator.

6)—Maximum dissolution of the extract in water.

The extract is taken up in demineralized water. Since the dissolution is not easy, the extract/water mixture is passed into an ultrasonic mixer in order to facilitate dissolution.

7)—Liquid/liquid extraction (aqueous phase containing the extract brought into contact successively with immiscible organic solvents). For each organic solvent, the volume corresponds to ⅔ of that of the aqueous phase (Vaq). Nevertheless, for each organic solvent the extraction is carried out three times, and therefore 2 Vaq are recovered for each organic solvent. The solvents used are the following:

Cyclohexane (Extract AmC)

Dichloromethane (Extract AmD)

Ethyl acetate (Extract AmA)

1-butanol previously saturated with water (extracting the flavonoid diglycosides of interest) (Extract AmB)

Characterization of the Extract AmB According to the Invention Phytochemical Analysis of the Extract AmB In order to be able to identify the compounds predominantly present in the butanolic extract AmB according to the invention, said extract is fractionated by vacuum liquid chromatography (stationary phase: C18-grafted silica, mobile phase: hydromethanolic solution with gradual increase in the methanol proportion);

For some of the sub-fractions obtained, they are fractionated again by exclusion chromatography on Sephadex™ LH 20 column.

For all the sub-fractions, they are fractionated again by reversed-phase semipreparative chromatography.

The predominant molecules purified are analyzed by UV spectrometry, high-resolution mass spectrometry (LC-ESI-QTOF) and nuclear magnetic resonance (1H and 2D NMR).

These analyses make it possible to identify the following compounds:

| 3-O-α-L-arabinopyranosyl(1->6)β-D-glucopyranosyl-myricetin (Molar mass: 612 g/mol, Empirical formula: $C_{26}H_{18}O_{17}$) ||
| --- | --- |
| UV spectrum ($\lambda_{max}$) | $^1$H NMR (500 MHz, Methanol-d4) δ |
| 204 nm 266 nm 359 nm | 3.13 (dd, J = 12.40, 1.14 Hz, 1H), 3.21 (dd, J = 10.07, 3.59 Hz, 1H), 3.43 (t, J = 8.90 Hz, 3 H), 3.54 (dd, J = 9.00, 7.78 Hz, 2 H), 3.63 (dd, J = 12.28, 5.95 Hz, 2 H), 3.69 (br dd, J = 12.44, 2.75 Hz, 1H), 3.92 (dd, J = 12.09, 1.49 Hz, 1H), 4.04 (d, J = 7.17 Hz, 1H), 5.19 (d, J = 7.86 Hz, 1H), 6.20 (d, J = 2.06 Hz, 1H) 6.40 (d, J = 2.06 Hz, 1H), 7.34 (s, 2 H) |

| 3-O-α-L-arabinofuranosyl(1->6)β-D-glucopyranosyl-myricetin (Molar mass: 612 g/mol, Empirical formula: $C_{26}H_{18}O_{17}$) ||
| --- | --- |
| UV spectrum ($\lambda_{max}$) | $^1$H NMR (500 MHz, Methanol-d4) δ |
| 207 nm 260 nm | 3.29 (dd, J = 9.61, 8.93 Hz, 1H), 3.42 (t, J = 9.50 Hz, 2 H), 3.45 (br dd, J = 11.22, 6.18 Hz, 2 H), |

-continued

| | |
|---|---|
| 357 nm | 3.51 (dd, J = 9.08, 8.09 Hz, 2 H), 3.56 (dd, J = 11.94, 5.00 Hz, 2 H), 3.66 (br dd, J = 11.94, 3.09 Hz, 2 H), 3.74 (dd, J = 5.84, 3.40 Hz, 1H), 3.81 (ddd, J = 6.03, 5.11, 3.20 Hz, 1H), 3.84 (br dd, J = 3.13, 1.53 Hz, 1H), 3.85 (dd, J = 10.91, 1.98 Hz, 1H), 4.76 (d, J = 0.92 Hz, 1H), 5.14 (d, J = 7.78 Hz, 1H), 6.20 (d, J = 1.98 Hz, 1H), 6.38 (d, J = 1.98 Hz, 1H), 7.26 (s, 2 H) |

3-O-α-L-rhamnopyranosyl(1->6)β-D-glucopyranosyl-myricetin
(Molar mass: 626 g/mol, Empirical formula: $C_{27}H_{30}O_{17}$)

| UV spectrum ($\lambda_{max}$) | $^1$H NMR (500 MHz, Methanol-d4) δ |
|---|---|
| 206 nm 262 nm 359 nm | 1.12 (br d, J = 6.18 Hz, 3 H), 3.28 (t, J = 9.60 Hz, 4 H), 3.40 (dd, J = 10.76, 5.84 Hz, 1H), 3.41 (t, J = 9.00 Hz, 1H), 3.50 (dd, J = 9.04, 8.13 Hz, 2 H), 3.55 (br dd, J = 9.44, 3.49 Hz, 1H), 3.63 (dd, J = 3.32, 1.60 Hz, 1H), 3.81 (dd, J = 10.99, 3.20 Hz, 1H), 4.53 (s, 1H) 5.08 (br d, J = 7.78 Hz, 2 H), 6.21 (d, J = 1.95 Hz, 1H), 6.40 (d, J = 2.06 Hz, 1H), 7.30 (d, J = 4.01 Hz, 2 H) |

3-O-α-L-arabinopyranosyl(1->6)β-D-glucopyranosyl-quercetin
(Molar mass: 596 g/mol, Empirical formula: $C_{26}H_{28}C_{16}$)

| UV spectrum ($\lambda_{max}$) | $^1$H NMR (500 MHz, Methanol-d4) δ |
|---|---|
| 202 nm 255 nm 354 nm | 3.14 (dd, J = 12.36, 1.44 Hz, 1H), 3.20 (dd, J = 8.97, 3.45 Hz, 1H), 3.34 - 3.38 (m, 1H), 3.34 - 3.38 (m, 1H), 3.42 (t, J = 8.80 Hz, 1H), 3.51 (dd, J = 9.54, 7.78 Hz, 1H), 3.61 (dd, J = 12.05, 6.15 Hz, 1H), 3.65 (d, J = 3.30 Hz, 1H), 3.69 (dd, J = 12.30, 3.14 Hz, 1H), 3.91 (dd, J = 12.17, 1.76 Hz, 1H), 4.05 (d, J = 7.03 Hz, 1H), 5.19 (d, J = 7.65 Hz, 1H), 6.21 (d, J = 2.01 Hz, 1H), 6.41 (d, J = 2.01 Hz, 1H), 6.88 (d, J = 8.28 Hz, 1H), 7.69 (d, J = 8.53, 2.38 Hz, 1H), 7.71 (d, J = 1.88 Hz, 1H) |

3-O-α-L-arabinofuranosyl(1->6)β-D-glucopyranosyl-quercetin
(Molar mass: 596 g/mol, Empirical formula: $C_{26}H_{28}C_{16}$)

| UV spectrum ($\lambda_{max}$) | $^1$H NMR (500 MHz, METHANOL-d4) δ |
|---|---|
| 202 nm 255 nm 359 nm | n.d. |

3-O-α-L-arabinopyranosyl(1->6)β-D-glucopyranosyl-kaempferol
(Molar mass: 580 g/mol, Empirical formula: $C_{26}H_{28}C_{15}$)

| UV spectrum ($\lambda_{max}$) | $^1$H NMR (500 MHz, METHANOL-d4) δ |
|---|---|
| 200 nm 241 nm 268 nm 349 nm | 3.17 (dd, J = 12.21, 1.53 Hz, 1H), 3.19 (dd, J = 8.85, 3.66 Hz, 1H), 3.41 (br t, J = 8.90 Hz, 3 H), 3.48 (br dd, J = 9.00, 7.78 Hz, 1H), 3.61 (dd, J = 12.21, 6.10 Hz, 1H), 3.63 - 3.66 (m, 1H), 3.69 (br dd, J = 12.36, 2.90 Hz, 1H), 3.90 (br dd, J = 11.90, 1.83 Hz, 1H), 4.06 (d, J = 7.02 Hz, 1H), 5.13 (br d, J = 7.63 Hz, 2 H), 6.12 (d, J = 1.83 Hz, 1H), 6.25-6.37 (m, 1H), 6.89 (br d, J = 8.85 Hz, 2 H), 8.10(d, J = 8.85 Hz, 1H) |

Demonstration of the Anti-Aging Effect of the Extract AmB According to the Invention Choice of Model The model chosen to demonstrate the technical effect of the Extract according to the invention is a model studying the activity of the collagenase enzyme. A purified collagenase is used and the degradation of its pro-fluorescent substrate is monitored by fluorimetry. This test makes it possible to demonstrate direct effects on the functionality of the enzyme itself.

Protocol

The anti-collagenase activity is evaluated using a commercially available kit (EnzCheck™ gelatinase/collagenase Assay Kit, Molecular Probes, reference E-12055).

This is a test based on a cell-free biochemical evaluation using a purified collagenase from a fungus (*Clostridium Histolyticum*) and a purified gelatin from porcine skin, purified type I collagen from bovine skin or purified type IV collagen from human placenta. The substrates (gelatin, collagen I or collagen IV) are conjugated to fluorescein, the fluorescence is revealed by digestion of the substrate by MMP and measured with a fluorimeter (Fluoroskan Ascent FL—Labsystem): excitation: 495 nm, emission: 545 nm. The increase in the fluorescence is proportional to the MMP activity. A decrease in this fluorescence is expected in the presence of anti-MMP active agents. The test is validated using a reference anti-MMP inhibitor provided in the kit, 1,10-phenanthroline, tested at 0.01% and 0.001%.

| Products tested | Concentration | Solubility |
|---|---|---|
| Armeria maritima (AmE) | 100 and 50 μg/ml | Stock solution at 10 mg/ml in DMSO |
| Armeria maritima (AmB) | 100 and 50 μg/ml | Stock solution at 10 mg/ml in DMSO |

The products are placed on a 96-well plate in the following manner:

| | Blank/control | Control | Blank test | Product |
|---|---|---|---|---|
| Extract to analyze | — | — | 80 μl | 80 μl |
| Reaction buffer 1X | 180 μl | 80 μl | 100 μl | — |
| Substrate | 20 μl | 20 μl | 20 μl | 20 μl |
| Enzyme | — | 100 μl | — | 100 μl |

The products are left to incubate for two hours at room temperature in darkness, then the fluorescence is determined (Excitation 495 nm; Emission: 515 nm). Each test is repeated three times. For each sample, the values are subtracted from the blank test. The percentage inhibition corresponds to the ratio of the mean of the collagenase activity obtained for each extract to the mean of the collagenase activity of the control group. The results obtained are given in the following table:

| Products tested | Concentration | Fluorescence | Standard deviation | Inhibition |
|---|---|---|---|---|
| Control 1 | — | 101.49 AU | 14.36 | — |
| 1,10-phenanthroline | 0.01% | 0.91 AU | 1.07 | 99% |
| 1,10-phenanthroline | 0.001% | 24.41 AU | 3.65 | 76% |
| AmB | 100 μg/ml | 49.04 AU | 16.06 | 52% |
| AmB | 50 μg/ml | 86.77 AU | 7.98 | 15% |
| Control 2 | — | 110.16 AU | 10.03 | — |
| 1,10-phenanthroline | 0.01% | 1.07 AU | 0.94 | 99% |
| 1,10-phenanthroline | 0.001% | 37.13 AU | 13.17 | 66% |
| AmE | 100 μg/ml | −0.02 AU | 0.06 | 100% |
| AmE | 50 μg/ml | 23.51 AU | 7.52 | 79% |
| DMSO | 1% | 91.62 AU | 13.07 | 17% |
| DMSO | 0.5% | 116.79 | 8.36 | −6% |

These results show that the extract according to the invention (AmB) has a significant effect at 100 μg/ml on inhibition of the anti-collagenase activity, albeit lower than that of the crude extract (AmE).

Evaluation of the Phototoxicity of the Extracts AmB According to the Invention and AmE According to the Prior Art This evaluation is carried out based on the experimental conditions of test no. 432, entitled "in vitro 3T3 NRU phototoxicity test" from the OECD guidelines for testing chemicals, regarding conditions related to culture kinetics and to the acceptable dosage limit for Chlopromazine (CPZ). This guideline describes a method for evaluating photo-cytotoxicity by the relative reduction in the viability of the cells exposed to the chemical product in the presence or absence of light.

Experimental Conditions Used

A pool of normal human fibroblasts of Caucasian type is used and amplified for five days in a 75 cm² flask in specific culture medium containing 10% FBS*. The cells are then seeded in culture wells of a 96-well plate (4 wells/condition), at 10 000 cells/well, in 200 µl of specific culture medium containing 10% FBS (Fetal Bovine Serum). 24 h after seeding, the cells are treated with the products for the test, prepared in EBSS (Earle's balance salt Solution) for one hour. At the end of this incubation, the cells are exposed (+irr) or not exposed (−irr) to a dose of 1 J/cm² of UVA, in the presence of the products being tested. At the end of this exposure, the cell layers are rinsed then brought back into contact with specific culture medium containing 2% of FBS. 24 h after this change, the cell viability is evaluated using the MTT method (colorimetric assay, visualized at 540 nm). The results are expressed as percentage viability relative to the control. The following parameters are deduced therefrom:

$EC_{50}$: Concentration of active agent inducing 50% toxicity (−irr) or phototoxicity (+irr)

PIF (photo-irradiation factor): $EC_{50(-irr)}/EC_{50(+irr)}$

PIF<2: No phototoxicity

2<PIF<5: Probable phototoxicity

PIF>5: Phototoxicity.

The evaluations of phototoxicity for each of the products tested are given in the following table:

|     | $EC_{50(-irr)}$ | $EC_{50(+irr)}$ | PIF |
| --- | --- | --- | --- |
| CPZ | 22.30 | 0.25 | 89.2 |
| AmB | 261.19 | 238.95 | 1.09 |
| AmE | 47.02 | 23.04 | 2.04 |

They demonstrate that, unlike the crude extract, the extract AmB according to the invention is not phototoxic and shows less toxicity than that measured for the crude extract AmE and for the reference CPZ.

Examples of Cosmetic Formulations Containing the Extract AmB

Dermo-Purifying Oil-in-Water Emulsion

| Water | q.s. 100% |
| --- | --- |
| Glycerol | 3% |
| Solagum ™AX | 0.3% |
| Montanov ™202 | 2% |
| Lanol ™ 99 | 7% |
| Cétiol ™OE | 3% |
| Lanol ™P | 0.25% |
| Sepiplus ™400 | 0.8% |
| Euxyl ™PE9010 | 1% |
| Sensiva ™PA40 | 0.5% |
| Extract AmB | 1% |
| Lactic acid at 20% | q.s. pH = 5.5 |

Anti-Sebum Oil-in-Water Emulsion

| Water | q.s.100% |
| --- | --- |
| Montanov ™202 | 3% |
| Montanov ™14 | 1.5% |
| Pelemol ™BB | 2% |
| Shea butter | 1.5% |
| Phytosqualane | 3% |
| Jojoba oil | 3% |
| C8-C10 triglyceride | 3% |
| DUB ISIP | 3% |
| D,L α-tocopherol | 0.1% |
| Solagum ™Tara | 0.6% |
| Extract AmB | 2% |
| Sorbic acid | 0.3% |
| Sodium hydroxide 48% | 0.07% |

Soothing Serum

| Sepimax ™Zen | 0.5% |
| --- | --- |
| Water | q.s. 100% |
| Butylene glycol | 2% |
| Aquaxyl ™ | 2% |
| Extract AmB | 1% |
| Montanox 20 | 1% |
| Phenoxyethanol & Ethylhexyl Glycerol | 0.80% |

SOLAGUM™AX: Mixture of acacia gum and xanthan gum, used as emulsifier;

MONTANOV™202 (INCI name: Arachidyl Alcohol & Behenyl Alcohol & Arachidyl Glucoside): Emulsifier;

LANOL™ 99: Isononyl isononanoate;

Cetiol™OE (INCI name: Dicaprylyl ether): Fatty phase;

LANOL™ P: Glycol palmitate;

SEPIPLUS™400 (INCI name: Polyacrylate-13 & Polyisobutene & Polysorbate 20): Polymeric thickener;

EUXYL™ PE9010 (INCI name: phenoxyethanol and ethylhexylglycerin): Preservative;

SENSIVA™PA40 (INCI name: Phenethyl Alcohol (and) Ethylhexylglycerin)/Antimicrobial agent;

MONTANOV™14 (INCI name: Myristyl Alcohol & Myristyl Glucoside): Emulsifier;

PELEMOL™BB: Behenyl Behenate;

SOLAGUM™Tara: Tara gum, used as emulsifier;

SEPIMAX™Zen (INCI name: polyacrylate crosspolymer-6): Thickener, emulsifier and stabilizer AQUAXYL™ (INCI name: Xylitylglucoside and Anhydroxylitol and Xylitol): moisturizing composition;

MONTANOX™ 20 (INCI name: Polysorbate 20): Emulsifier of oil-in-water type.

The invention claimed is:

1. A process for preparing an aqueous-alcoholic extract originating from a biomass of aerial parts of a plant of the Plumbaginaceae family, comprising the following successive steps:
    at least one step A) of maceration in an aqueous-alcoholic solution of said aerial parts of said plant of the Plumbaginaceae family, for which the alcohol used is chosen from methanol or ethanol, in order to obtain an aqueous-alcoholic suspension therefrom;

at least one step B) of filtration of said aqueous-alcoholic suspension obtained in step A), in order to separate an aqueous-alcoholic extract from the plant biomass;

a step C) of drying said aqueous-alcoholic extract obtained in step B), in order to obtain a dry residue therefrom;

a step D) of dissolving said dry residue obtained in step C) in water, in order to obtain an aqueous phase $\varphi_0$;

at least one first step $E_1$) of liquid-liquid extraction by bringing said aqueous phase $\varphi_0$ obtained in step D) into contact with a nonpolar organic solvent, in order to obtain, after separation of the immiscible phases, a new aqueous phase $\varphi_1$;

at least one second step $E_2$) of liquid-liquid extraction by bringing said aqueous phase $\varphi_1$ obtained in step $E_1$) into contact with a polar aprotic organic solvent, in order to obtain, after separation of the immiscible phases, a new aqueous phase $\varphi_2$;

at least one third step $E_3$) of liquid-liquid extraction by bringing said aqueous phase $\varphi_2$ obtained in step $E_2$) into contact with a polar protic organic solvent chosen from alkanols comprising from four to eight carbon atoms, or alkanediols comprising from four to eight carbon atoms, in order to obtain, after separation of the immiscible phases, said expected alcoholic extract and a new aqueous phase $\varphi_3$.

2. The process as defined in claim 1, for which, during step A), the alcohol used is ethanol.

3. The process as defined in claim 1, for which the ratio by volume of alcohol to water in the aqueous-alcoholic solution used in step A) is between 60% and 90%.

4. The process as defined in claim 1, also comprising, prior to step A):

a step $A_0$) of harvesting said aerial parts of said plant of the Plumbaginaceae family, in order to obtain a biomass therefrom which is subsequently subjected to step A).

5. The process as defined in claim 4, also comprising:
a step $A_1$) of drying said biomass obtained in step $A_0$), in order to obtain a dried biomass therefrom, which is subsequently subjected to step A).

6. The process as defined in claim 4, also comprising:
a step $A_2$) of grinding said biomass obtained in step $A_0$) or said dried biomass obtained in step $A_1$), in order to obtain said biomass therefrom which is subjected to step A).

7. The process as defined in claim 6, also comprising:
a step $A_3$) of pulverizing-grinding said ground biomass obtained in step $A_2$), in order to obtain said biomass therefrom which is subjected to step A).

8. The process as defined in claim 1, for which, during step $E_1$), said nonpolar organic solvent used is hexane or cyclohexane.

9. The process as defined in claim 1, for which, during step $E_2$), said polar aprotic organic solvent used is dichloromethane or ethyl acetate.

10. The process as defined in claim 1, wherein said at least one step $E_2$) consists of a step $E_{2a}$) of liquid-liquid extraction by bringing said aqueous phase $\varphi_1$ obtained in step $E_1$) into contact with the dichloromethane, in order to obtain, after separation of the immiscible phases, a new aqueous phase $\varphi_{2a}$; followed by a step $E_{2b}$) of liquid-liquid extraction by bringing said aqueous phase $\varphi_{2a}$ obtained in step $E_{2a}$) into contact with the ethyl acetate, in order to obtain, after separation of the immiscible phases, said aqueous phase $\varphi_2$.

11. The process as defined in claim 1, for which, during step $E_3$), said polar protic organic solvent used is 1-butanol.

12. The process as defined in claim 1, for which, during steps $E_1$), $E_2$) and $E_3$), the ratio by volume of organic solvent to, respectively, the aqueous phases $\varphi_0$, $\varphi_1$ and $\varphi_2$, is between ½ and 1/1.

13. The process as defined in claim 1, wherein said plant of the Plumbaginaceae family belongs to the genus *Armeria* Willd.

14. The process as defined in claim 13, wherein said plant belonging to the genus *Armeria* Willd is from the species *Armeria maritima*.

15. The process as defined in claim 1, also comprising:
a step F) of evaporation of the alkanol or of the alkanediol of the alcoholic extract obtained in step $E_3$), in order to obtain a dry extract therefrom.

16. The process as defined in claim 1, for preparing a butanolic extract originating from a biomass of aerial parts of *Armeria maritima*, comprising the following successive steps:

a step $A_0$) of harvesting said aerial parts of *Armeria maritima*, in order to obtain therefrom harvested material of said aerial parts;

a step $A_1$) of drying said harvested material obtained in step $A_0$);

a step $A_2$) of grinding said harvested material dried in step $A_1$), in order to obtain a ground material of said dried harvested material;

if necessary, or if desired, a step $A_3$) of pulverizing the ground material obtained in step $A_2$), in order to obtain a powder of said dried harvested material;

at least one step A) of maceration, in an aqueous-ethanolic solution having a ratio by volume of ethanol/water equal to 80/20, of said powder obtained in step $A_3$, in order to obtain an aqueous-ethanolic suspension therefrom;

at least one step B) of filtration of said suspension obtained in step A), in order to separate an aqueous-ethanolic extract therefrom;

a step C) of drying said aqueous-ethanolic extract obtained in step B), in order to obtain a dry residue therefrom;

a step D) of dissolving said dry residue obtained in step C) in water, in order to obtain an aqueous phase $\varphi_0$;

at least one step $E_1$) of liquid-liquid extraction, by bringing said aqueous phase $\varphi_0$ obtained in step D) into contact with cyclohexane at a ratio by volume of cyclohexane/aqueous phase $\varphi_0$ equal to ⅔, in order to obtain, after separation of the immiscible phases, a new aqueous phase $\varphi_1$;

at least one step $E_{2a}$) of liquid-liquid extraction by bringing said aqueous phase $\varphi_1$ obtained in step $E_1$) into contact with dichloromethane at a ratio by volume of dichloromethane/aqueous phase $\varphi_1$ equal to ⅔, in order to obtain, after separation of the immiscible phases, a new aqueous phase $\varphi_{2a}$;

at least one step $E_{2b}$) of liquid-liquid extraction by bringing said aqueous phase $\varphi_{2a}$ obtained in step $E_2$) into contact with ethyl acetate at a ratio by volume of ethyl acetate/aqueous phase $\varphi_{2a}$ equal to ⅔, in order to obtain, after separation of the immiscible phases, a new aqueous phase $\varphi_{2b}$;

at least one step $E_3$) of liquid-liquid extraction by bringing said aqueous phase $\varphi_{2b}$ obtained in step $E_{2b}$) into contact with 1-butanol saturated with water at a ratio by volume of 1-butanol/aqueous phase $\varphi_2$ equal to ⅔, in order to obtain, after separation of the immiscible phases, said expected butanolic extract and a new aqueous phase $\varphi_3$.

\* \* \* \* \*